United States Patent
Lai et al.

(10) Patent No.: US 12,144,530 B2
(45) Date of Patent: Nov. 19, 2024

(54) ORTHOPEDIC IMPLANT SYSTEM FOR VARIABLE ANGLE LOCKING HAVING ENGINEERED MATING THREAD ENGAGEMENT

(71) Applicant: ORTHO SOLUTIONS HOLDINGS LIMITED, Lakewood, CO (US)

(72) Inventors: Geoff Lai, Lakewood, CO (US); Kevin Stamp, Chapeltown Sheffield (GB); Dustin Ducharme, Littleton, CO (US); Andrew Leither, Akron, OH (US)

(73) Assignee: ORTHO SOLUTIONS HOLDINGS LIMITED, Lakewood, CO (US)

( * ) Notice: Subject to any disclaimer, the term of this patent is extended or adjusted under 35 U.S.C. 154(b) by 515 days.

(21) Appl. No.: 17/289,543

(22) PCT Filed: Nov. 12, 2019

(86) PCT No.: PCT/US2019/060895
§ 371 (c)(1),
(2) Date: Apr. 28, 2021

(87) PCT Pub. No.: WO2020/102179
PCT Pub. Date: May 22, 2020

(65) Prior Publication Data
US 2021/0393303 A1    Dec. 23, 2021

Related U.S. Application Data

(60) Provisional application No. 62/760,504, filed on Nov. 13, 2018, provisional application No. 62/760,521, filed on Nov. 13, 2018.

(51) Int. Cl.
*A61B 17/80* (2006.01)
*A61B 17/86* (2006.01)

(52) U.S. Cl.
CPC ...... *A61B 17/8057* (2013.01); *A61B 17/8605* (2013.01)

(58) Field of Classification Search
CPC .................................................. A61B 17/8057
See application file for complete search history.

(56) References Cited

U.S. PATENT DOCUMENTS

| | | |
|---|---|---|
| 2010/0100134 A1 | 4/2010 | Mocanu |
| 2014/0018862 A1 | 1/2014 | Koay et al. |
| 2014/0066998 A1 * | 3/2014 | Martin ................. A61B 17/863 |
| | | 606/286 |
| 2016/0310182 A1 | 10/2016 | Sixto et al. |
| 2018/0271573 A1 | 9/2018 | Martin et al. |
| 2019/0290338 A1 * | 9/2019 | Bosshard ............... A61B 17/86 |
| 2019/0328430 A1 * | 10/2019 | Bosshard ........... A61B 17/8057 |

* cited by examiner

*Primary Examiner* — Olivia C Chang
(74) *Attorney, Agent, or Firm* — Hudak, Shunk & Farine Co. LPA

(57) ABSTRACT

The invention relates to an orthopedic implant system comprising an implant including a threaded aperture which receives either a first non-locking bone fastener or a second threaded variable axis locking fastener. The threaded aperture includes interruptions to form sections having a thread segment. The variable axis locking fastener has a threaded head configured to cause the threads to wedge against the female threads of the aperture as the fastener is tightened into the aperture in an off-axis orientation. In a further embodiment, the aperture includes a concentric annular groove to form flexible threaded tines.

23 Claims, 9 Drawing Sheets

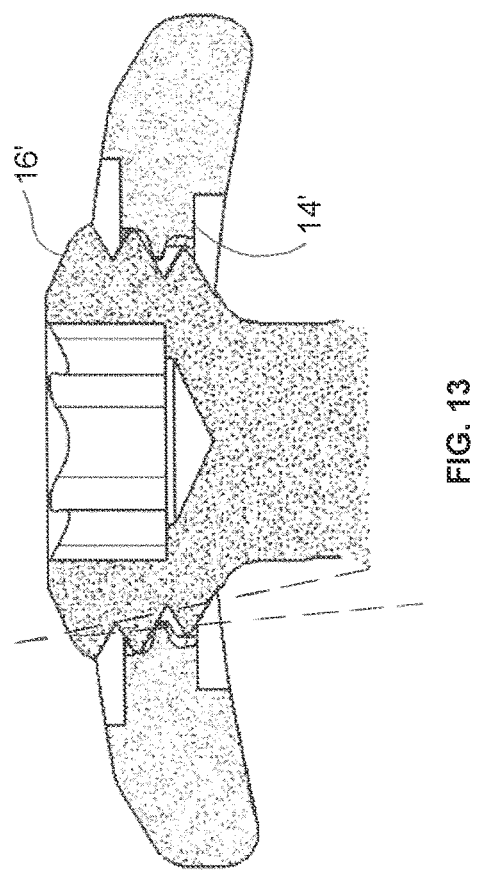
FIG. 13
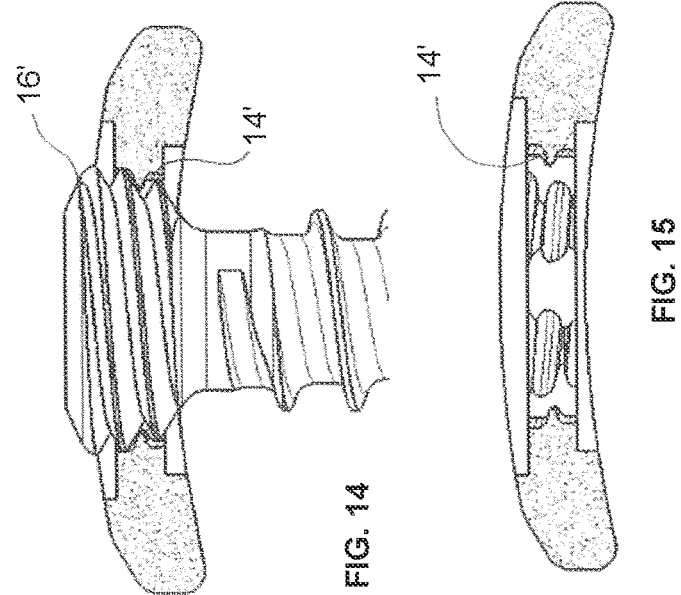
FIG. 14
FIG. 15

ORTHOPEDIC IMPLANT SYSTEM FOR VARIABLE ANGLE LOCKING HAVING ENGINEERED MATING THREAD ENGAGEMENT

FIELD OF THE INVENTION

The invention relates to an orthopedic implant system which includes fasteners for fixation to bone. More particularly, the implant system has an implant having an aperture that can accept either a non-threaded non-locking fastener, or a threaded locking fastener that can be locked relative to the implant at a perpendicular axis or at an oblique angle within a conical orientation up to 15°, 20°, 25° or even 30° off that axis.

BACKGROUND OF THE INVENTION

Orthopedic medicine has evolved implant systems including implants, such as bone plates, nails, and cages that are used with fasteners such as pegs, and screws, for internal fixation of bones. These orthopedic systems include a bone plate, configured to be attached to one or more bones or bone segments, for example, spanning a fracture or osteotomy line. These bone plates generally include a plurality of apertures or holes through which bone screws and/or bone pegs are inserted for engaging the underlying bone and to assemble a "construct" which includes the plate, screws and the bone. The engagement mechanisms for securing the plate to the bones include both screws which lock relative to the plate, (i.e. "locking" screws) and screws which do not lock relative to the plate, (i.e. "non-locking" screws). Both types of screws typically have a head and a shaft including cortical bone threads to permit the screw shaft to be screwed into and fixed relative to the bone which underlays the plate surrounding the plate aperture. The type of fixation will affect the forces that are applied to the bone by the implant system, which in turn will influence the physiological response of the biological system.

Typically, in the case of locking screws, the plate aperture includes a set of internal or female threads and the screw head includes a set of external or male threads that mate with the female threads in a cooperation at a fixed orientation to accommodate typical fracture patterns. In another example, the bone plate systems can include locking screws, which can be configured for insertion at an orientation selected by the acting surgeon, for example, to capture a bone fragment that does not follow a typical fracture pattern. These systems are known as poly-axial or variable locking systems. An advantage of "locked plating" systems is that they do not require the bone plate to be compressed to the bone. Rather, in this construct, the interface formed between the bone plate and the locking screws can eliminate the need for compression between the plate and the bone by acting to stabilize the plate to the screw.

In other instances, it may be preferable to use a bone/implant construct in which the fasteners (i.e. screws) are only fixed in the bone, but which include a head that resides in an aperture in the implant so as to draw the plate toward the bone. Unlike "locked plating" systems, "non-locked plating" systems rely on the axial force toward the bone of the bone screw head in the plate aperture when the screw is inserted through the bone plate and tightened, and the plate typically spans at least two screws to support the bone to bone interface between them.

The present invention provides an improved implant fixation system which balances the stability afforded by the implant system with ease of use for the surgeon, and a construct with a wide variety of fixation, orientation and compression characteristics in a single system set.

SUMMARY OF THE INVENTION

The invention relates to an orthopedic implant system comprising an implant including a first surface and an opposing second surface with at least one compound threaded aperture there between, and a first bone fastener which is a non-locking fastener and a second fastener which is a variable axis locking fastener, and the at least one threaded aperture can accept either the first or the second fastener to secure the implant to a bone. The aperture is a compound recess having a first and/or second counterbore section joined to an annulus that includes internal threads and which includes a plurality of recesses or thread interruptions so as to form interrupted threaded areas. The head of the non-locking fastener includes a tapered rounded portion that rides on the threads of the aperture. The variable axis locking fastener has a tapered head which includes male threads, and the female threads of the aperture and the male threads of the fastener are configured to have a specifically engineered mismatch which causes the male threads to wedge against the female threads as the fastener is tightened into the aperture in an off-axis orientation.

More specifically, in a first embodiment, the invention relates to poly-axial fastener locking systems comprising an orthopedic implant, such as an orthopedic plate, having at least one compound fastener aperture with a cylindrical annulus having corresponding threads having a thread crest that describes a cylindrical helical shape, and that receives either 1) a tapered non-locking fastener, such as a screw, having a smoothly rounded head including a lowered tapered portion which rides on the threads or 2) a locking fastener, such as a screw, having a tapered head with multi-lead tapered threads having threads crests that describe a conical helical shape, and that have a mismatched thread configuration relative to the internal threads of the aperture.

In a second embodiment, the annulus portion of the aperture has a diameter that decreases in diameter from the top surface toward the bottom surface of the plate. This configuration can comprise a taper including a conical configuration, or a hemispherical configuration, or a concave configuration that is more generally inwardly rounded.

In all cases, the outer thread crest of the screw head describes a configuration that differs from the configuration of the aperture, such as differing shapes and/or differing degrees of angulation on a tapered conical surface. In addition, in all cases, it is preferable that the internal threads on the annular portion of the aperture have a sharper angled thread crest than the thread recess of the external screw head threads. Thus, the plate's male thread form is 30°+/−5° in cross-section as compared to the screw head's female thread cut-out, which is 60°, +/−10°, so as to facilitate off-axis threading without damaging the thread. The locking screw head threads are on a decreasing diameter, such as a conical taper to facilitate variable angle engagement and to prevent the screw from being advanced all the way through the plate. The locking screw locks in at a pre-determined orientation which aligns with the central axis of the aperture or at an orientation that is off-axis by up to 15° each way in a conical distribution. The threaded aperture includes multiple radially symmetrically distributed lobed thread interruptions so that the threads of the screw head will pick up at one of these interruptions. In at least the first and the second embodiment of the invention, the interruptions are recesses formed in the vertical threaded surfaces of the threaded annulus which form complex three-dimensional non-discrete sections that include a thread segment. As used herein "non-discrete" refers to the fact that the threaded annulus has a pre-existing topography that varies in the direction of the central axis of the aperture and the interruption has the effect of interrupting the thread valley and the thread crest to differing degrees along a vertical line taken along the annular surface. The aperture is a compound recess including a narrow necked portion that forms the annulus and the underside of the aperture includes a widened mouth area such as a counterbore or chamfer, to accommodate the neck of the screw in wide angle insertions. The underside of the locking screw head includes a cutting feature to counterbore any bone that might inhibit the full engagement of the screw.

The top surface of the screw includes a torque driving recess that tapers as it descends into the screw and the top surfaces that extend away from this recess are smoothly rounded downward into the head side portions that include the thread cut outs.

In a further embodiment, the bone facing surface of the implant includes a recess that is concentric to the aperture and the interruptions in the threads connect so as to form flexible tines of threads between the interruptions.

BRIEF DESCRIPTION OF THE DRAWINGS

FIG. 13 is a detail showing the cross-section of a second embodiment of the implant of the present invention;

FIG. 14 is a side view of the implant system of FIG. 13 showing the screw in side view and the implant as a partial section;

FIG. 15 is a cross section of the plate of FIG. 14;

DETAILED DESCRIPTION OF THE INVENTION

Figure 1:
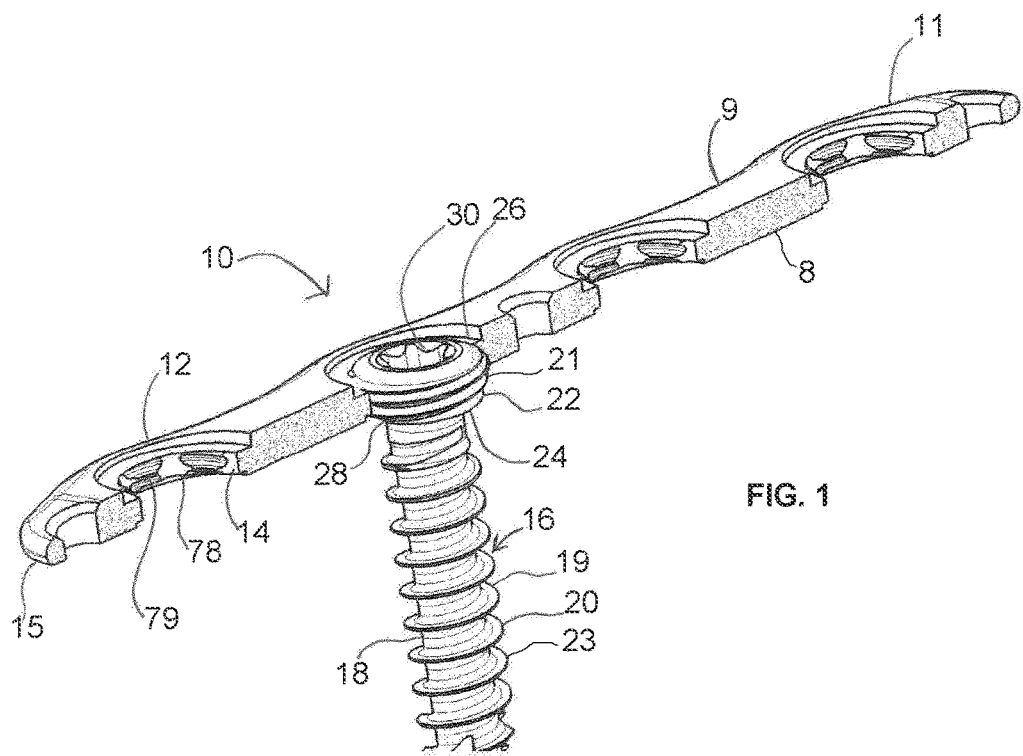
FIG. 1 shows a top side view of the orthopedic implant system of the present invention having a variable axis locking screw in a normal orientation in an implant which is shown in cross-section.

The present invention relates to an orthopedic implant system 10 which includes an implant 9, such as a member having two major opposing, and typically co-extending, or concentric surfaces, which will be referred to as a "top surface" 11, meaning the surface intended to face out relative to the affected bone, and a "bottom surface" 8, meaning the surface that is configured to contact, or face toward the affected bone and a side edge 15 including a long edge 9. Plates have typically been configured in a curved blade-like configuration where the curve is meant to accommodate the long radiused surfaces of bone they are meant to support, such as the femur, fibula, radius or humerus. However, as orthopedic implants have become increasingly sophisticated, the outlines and profiles have evolved in more complex shapes with generalized curves or bends to accomplish certain medical goals. In addition, sometimes implants will also include portions that are intended to project into the bone, rather than sitting against it, and these areas tend to be more cylindrical and less "plate-like" in order to support the bone from the intramedullary channel.

The implant, or plate 12, has at least one threaded compound aperture 14 which includes a necked area or annulus 13 having internal or female threads 17. More typically the implant has multiple apertures 14, which in a first embodiment, has a cylindrical configuration in the annular portion, meaning that throughout at least 50%, and preferably 75%, and most preferably 85% of the depth of the annulus 13 as measured from one surface of the plate to the opposing surface there is a constant major diameter in the annulus portion of the aperture and a constant minor diameter in the annulus portion of the aperture (as defined by a line at which intersections the edges of the major diameter and the minor diameter shown in cross-section or alternatively, the threads, or more specifically, the thread crest follow a cylindrical helical path for at least 120° radially, and preferably 180°, and preferably 270° radially, depending on whether the threads are single or multiple leads, and preferably double lead). This means that the thread edges at the major diameter subscribes a portion of a cylinder for at least a portion of the height of the aperture, likewise, so may the thread root. The aperture 14 includes one or more counterbores or chamfers 33 joined to the annulus 13, to allow for a wider angulation or to accommodate the screw head member 22. The internal thread 17 is preferably a double lead thread which will lock with less thread deformation since the locking head does not seat fully in the aperture as the bottom threads are not in the way try to force the screw back on-axis (and therefore causes less need for thread deformation in that bottom-left corner).

In a further embodiment of the variable locking system of the present invention, the annulus portion 13 of the plate aperture 14 as considered at the thread root or thread crest, has a diameter that decreases along the central axis of the aperture from the top of the plate to the bottom of the plate. In particular, the configuration of the plate aperture differs from the configuration of the screw head where both configurations are defined at the thread crests. This could mean tapering conical configurations at differing angles, such as the screw head having a taper of from 5° to 30°, and preferably from 12° to 20° (or 15°+/−7° or 5°) and the plate aperture has a taper that is from 5° to 40°, and preferably 25° to 35° (or 10°+/−7° or 5°), in difference as measured by the angle between a line at the thread crest and the central longitudinal axis of the relative configuration, with the thread of the aperture forming a greater angle of from 25° to 60°, and preferably from 30° to 50° (or 40°+/−7° or 5°). Alternatively, the differing configurations could be rounded or hemispherical shapes of differing diameters.

The invention further includes a first fastener, which is variable locking screw 16 which has a shaft 18 including a distal portion 19 that has a cortical bone thread 20 extending from the shaft 18 which defines the minor diameter of the cortical thread to the thread crest 23 which defines the major diameter of the cortical thread, and a proximal portion 21 that includes a head member 22 which is convexly rounded, tapered or conical in shape and which includes external or male threads 24. The threads 24 run from a top surface 26 of the screw head member 22 to a necked portion 28 which joins the head member 22 to the shaft 18. At the distal portion 25 of the head member 22, the screw includes at least one, and preferably two or three cutting flutes 29. The distal portion 19 of the screw can also include cutting flutes. The proximal portion 27 of the screw 16 includes a top surface 26 of the screw, which has a torque driving recess 30 which can be a hexalobe shape, and preferably can include an internal taper to enable a press fit with a mating torque driver head. The cutting flutes are provided to bore a countersink into the bone to accommodate a deeper screw head in a thinner plate. Thus, the countersink helps to minimize prominence above the bone by sinking part of the screw head below the bottom surface of the plate into the bone and to reduce the number of operative steps, the cutting flutes would help automatically countersink any bone that gets in the way.

Figure 2:
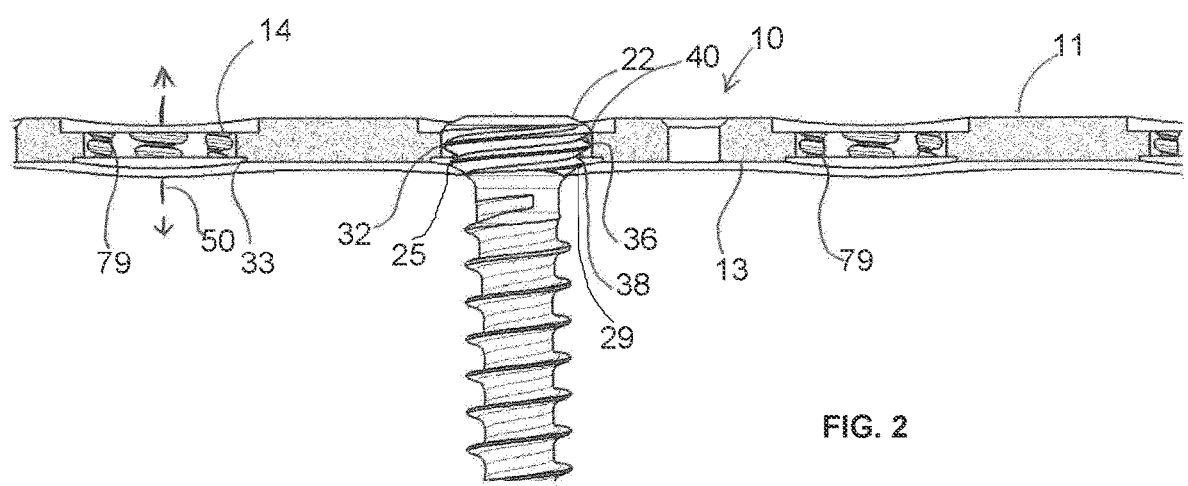
FIG. 2 shows a side cross-sectional view of the orthopedic implant system of FIG. 1.
Figure 8:
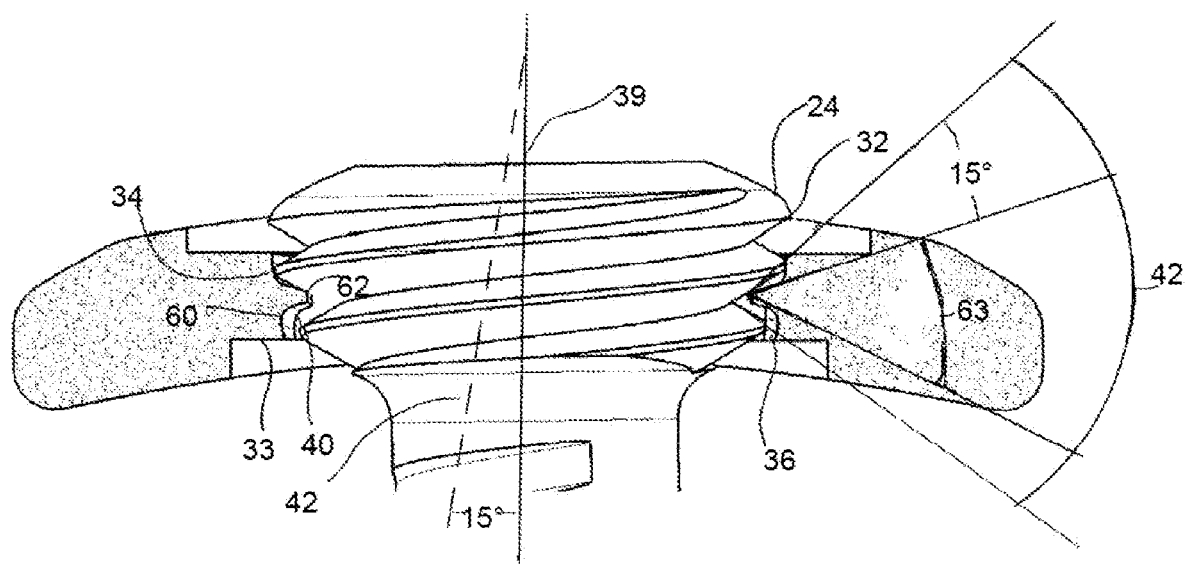
FIG. 8 a detail of the variable locking screw shown at a normal axis orientation in an aperture of the implant of the present invention in cut-away form and illustrating the thread angle mismatch.

The locking threads 24 of the head member 22 are preferably dual lead threads, with a start point 180° apart, and have a major diameter 32 and a minor diameter 34 with a locking thread crest 36 at the junction of a bottom thread face 38 and a top thread face 40 which together define a thread cut-out angle 42 as shown in FIG. 8. The screw head member 22 configuration includes a decreasing diameter, or more specifically, a taper, meaning that lines connecting the major diameters converge toward the screw axis in the distal direction and that lines connecting the minor diameters converge toward the screw axis in the distal direction as can be seen in FIG. 2. A taper angle A can be defined between the longitudinal axis 39 of the screw and the outer diameter at the crest of the locking threads of the screw head member 22 such that the taper angle represents one half of the total taper with the same being true for the taper angle of the aperture. Although any suitable taper angle A can be used, suitable taper angles A can be between about 2° and about 35°, and more particularly between about 5° and about 25°, such as about 15°+/−5°. Similarly to the corresponding definition of the cylindrical annulus, the screw head is considered tapered as marked by the following concepts: the edge of the thread or threads, i.e., the thread crest, or the edge of the minor diameter, i.e., the thread root, in the case of multiple lead threads at the major diameter subscribe a portion of a cone, and define for at least 120°, and preferably at least 180°, or 270° or 360° or for an at least 75% of an entire diameter or preferably for at least a fully turn of the screw head, the threads follow the path of a helical cone.

Figure 7:
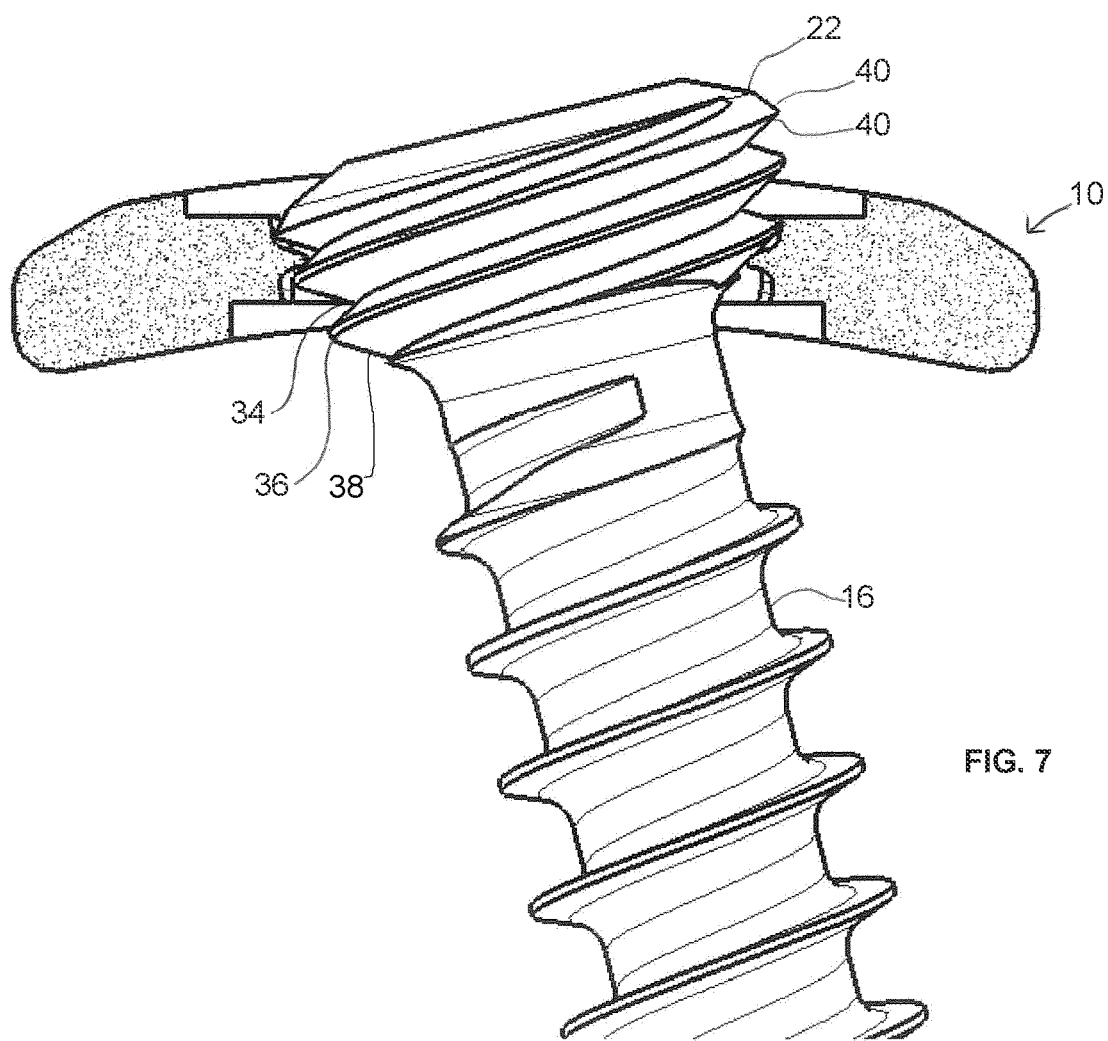
FIG. 7 is a detail of the variable locking screw shown at an oblique axis orientation in an aperture of the implant of the present invention in cut-away form.
Figure 9:
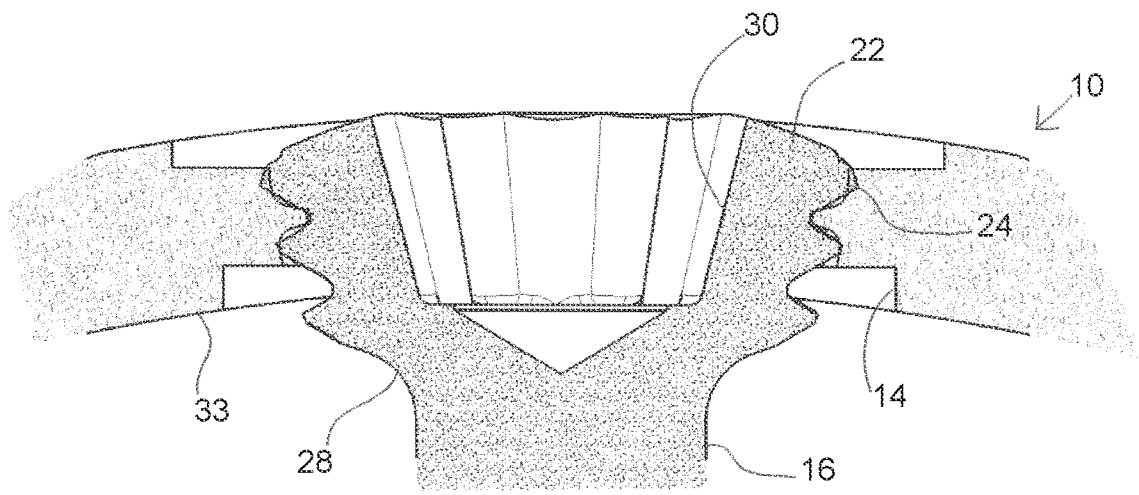
FIG. 9 is a detail in cross-section of the torque driving recess of the implant of the present invention.
Figure 10:
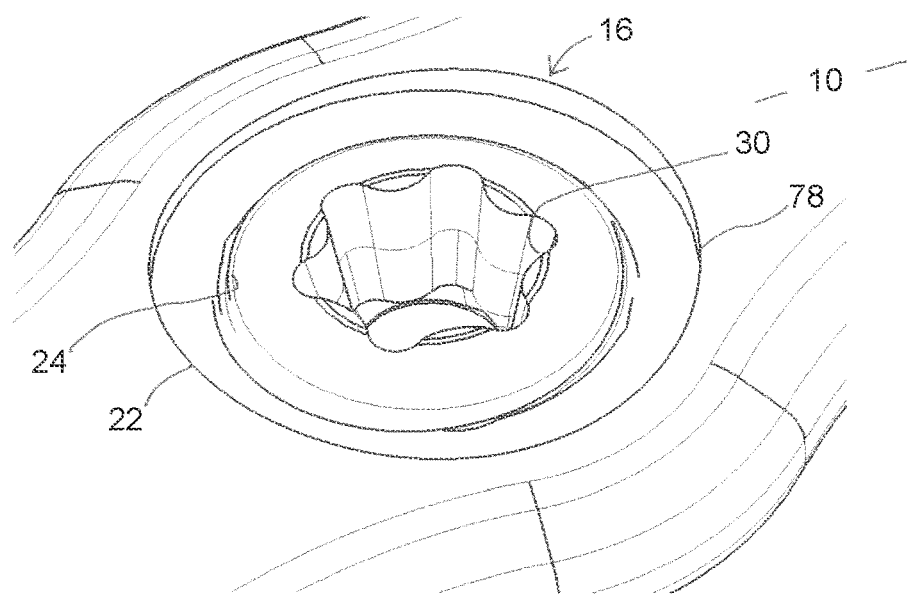
FIG. 10 is a top side view of the of the torque driving recess of the implant of FIG. 9.

In contrast, the annulus 13 of the plate aperture 14 has a deliberately mis-matched configuration that differs from the configuration of the screw head, such as being generally cylindrical with a tapered screw head (aside from any chamfers or other reliefs), and has a diameter that is intermediate the widest major diameter of the screw head 22 and the narrowest major diameter 32. In a first embodiment, the threads 17 of the plate 12 follow a cylindrical (non-tapered) helical path while the thread 24 of the screw head member 22 follows a tapered helical path that increases in diameter as it travels up proximally on the screw head 22. Thus, in a mating cooperation the trailing (upward) surfaces of the plate threads support the screw while the crests of the screw threads press radially outward on the plate's thread major as the screw's advanced until it binds as is shown in FIG. 7. The present invention utilizes a tapered locking screw head member and a cylindrical threaded locking aperture, which has the advantage over a system using a tapered locking aperture which tends to re-orient an off-axis screw orientation back to center.

In a further embodiment, the configuration of the annulus of the aperture varies from the configuration of the screw head in that both may have a decreasing diameter, but which decreases at a different rate in the direction of the central axis from the top to the bottom respectively. In addition, the thread angle of the aperture and of the screw head differ so as to present an intended mis-match of 15 degrees in either direction between the mating thread surfaces. This allows for 30 degrees of conical freedom in the angulation but still provides for locking by means of the tapered mismatch on the thread crest of the plates onto the thread valley of the screw.

As illustrated in FIG. 2, the threaded apertures 14 can define a longitudinal axis 50 extending through the threaded aperture 14 between the first surface 11 and the second surface 8 of the bone plate 12. The longitudinal axis 50 can represent the "centerline" of the threaded aperture 14 and is therefore dependent on the orientation in which the threaded aperture 14 is formed in the bone plate 12. In various examples, the threaded aperture 14 can be formed in the bone plate 12 such that it extends generally perpendicular to the first surface 11 and the second surface 8, or the threaded aperture 14 can be formed in the bone plate 12 such that it extends at an oblique or non-perpendicular angle relative to the first surface 11 and the second surface 8. Regardless of the orientation of the threaded aperture 14, the longitudinal axis 50 defines only one of the axes along which the variable locking fastener can be inserted. Thus, the threaded aperture 14 and the locking fastener 16 can define a "variable axis locking" or "polyaxial" fastening system wherein the locking fastener 16 can be inserted into the threaded aperture 14 in a plurality of different insertion angles relative to the longitudinal axis 50 of the aperture while achieving a locking engagement between the thread head 22 and the threaded aperture 14. An example of this variable axis locking capability is illustrated in FIG. 7, wherein the elongate shaft 18 of the locking fastener 16 does not extend along the longitudinal axis 50 of the corresponding threaded aperture 14, but instead forms an angle with the longitudinal axis 50 while maintaining a locking connection between the externally threaded head member 22 and the internally threaded aperture 14.

FIG. 8 illustrates the threads 17 of the plate aperture 14. The threads can be thrust threads having a truncated V-shape defining a series of roots 60 and crests 62 and having an internal thread angle T1 at 63. The internal thread angle T1 is 60°+/−20°, and preferably +/−15° or 10°. A thread height H1 of the threads of the internally threaded surface 14 can be defined between one of the roots 60 and an adjacent one of the crests 62. The roots 60 and/or the crests ° can be truncated to avoid the formation of a "sharp" V-shape, or a trough. A perfectly sharp 60° V-thread generally includes a thread height equal to about 0.866 of the pitch. However, with truncated threads, the thread height decreases. In an example, the thread height H1 can be between about 0.008 inches and about 0.015 inches, such as about 0.0118 inches. The screw threads have an external thread angle T2, 42, at the thread crest which is about 30°+/−20° preferably +/−15° or 10°. T1 is different than T2, and is preferably 30°. preferably +/−15° or 10° inclusively (meaning including both sides of the thread crest or trough.)

Figure 16:
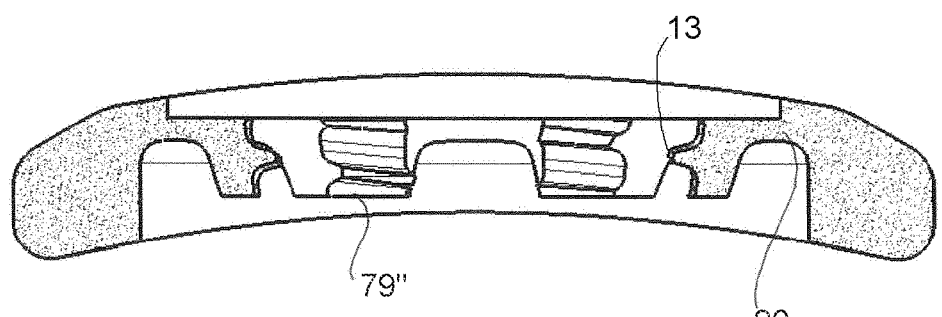
FIG. 16 illustrates a cross-section of an implant aperture for a third embodiment of the invention.
Figure 17:
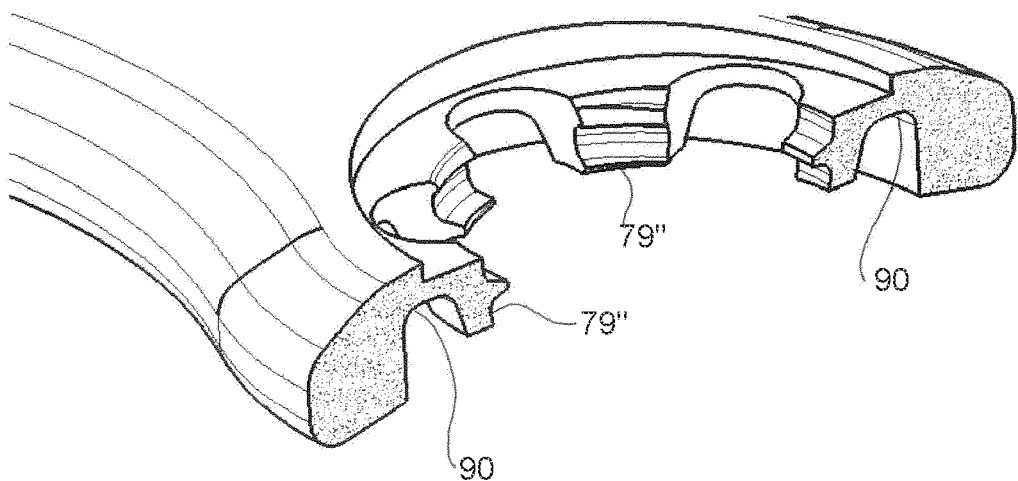
FIG. 17 is a top edge view of a section of the aperture of FIG. 16.

FIG. 16 illustrates that the angle T2 of the screw head has a differential on both sides of the crest (i.e. the leading and trailing surfaces) which are smaller than the corresponding thread trough on the female threads of the screw head. The difference on one of the two sides T3 is equal to the one half of the available conical angle of variability for the variable locking aspect of the screw in the aperture.

Figure 3:
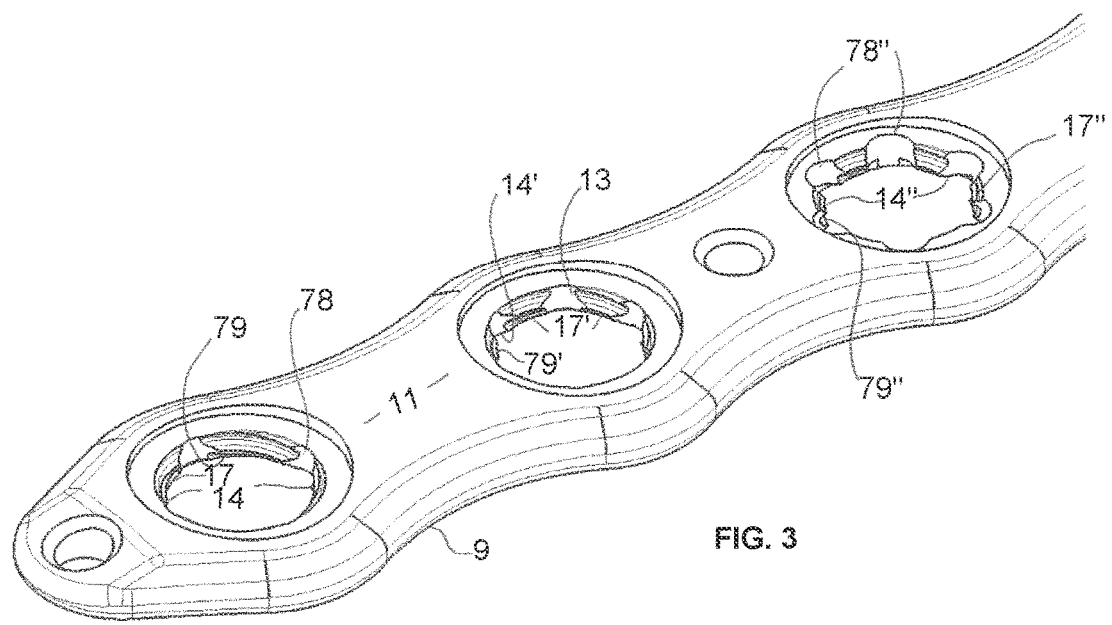
FIG. 3 shows top side view of an implant with three embodiments of the aperture of the present invention.
Figure 4:
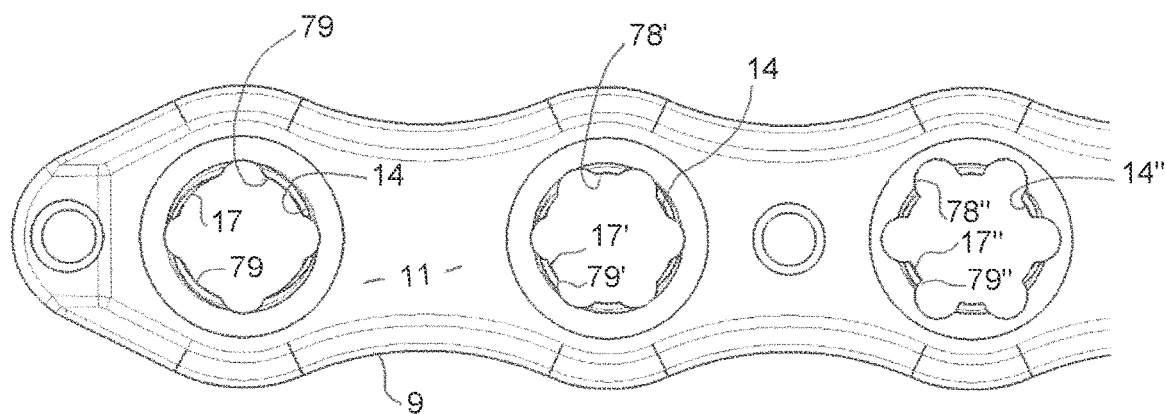
FIG. 4 is a top view of the implant of FIG. 3.
Figure 5:
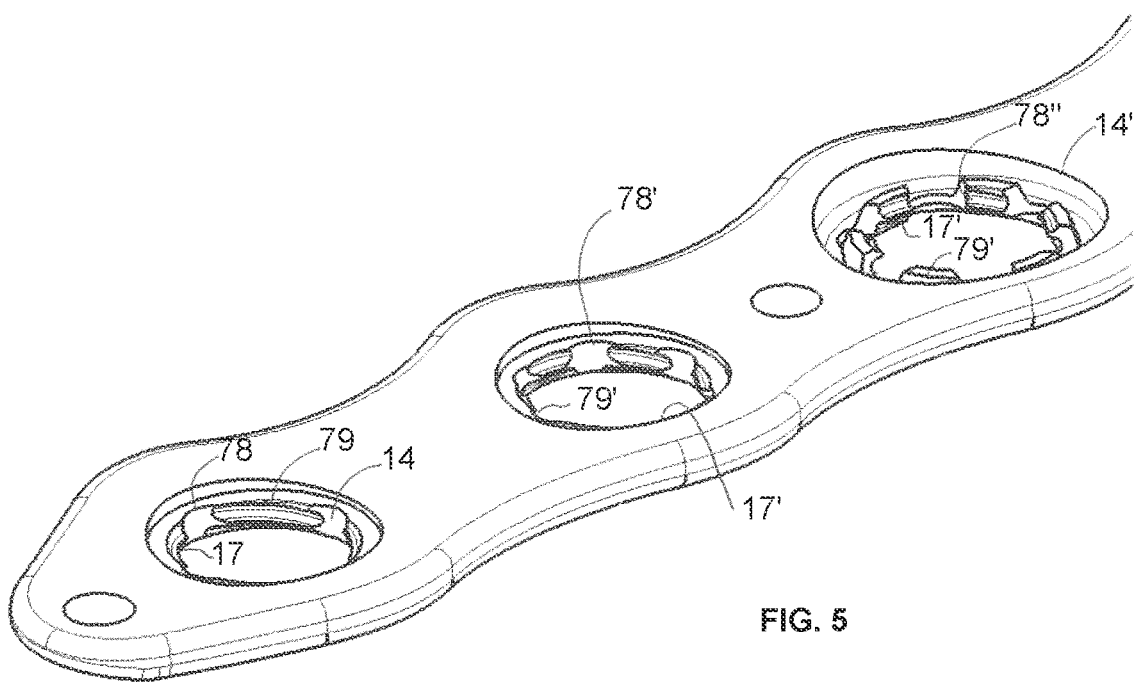
FIG. 5 is bottom view of the of the implant of FIG. 4.
Figure 6:
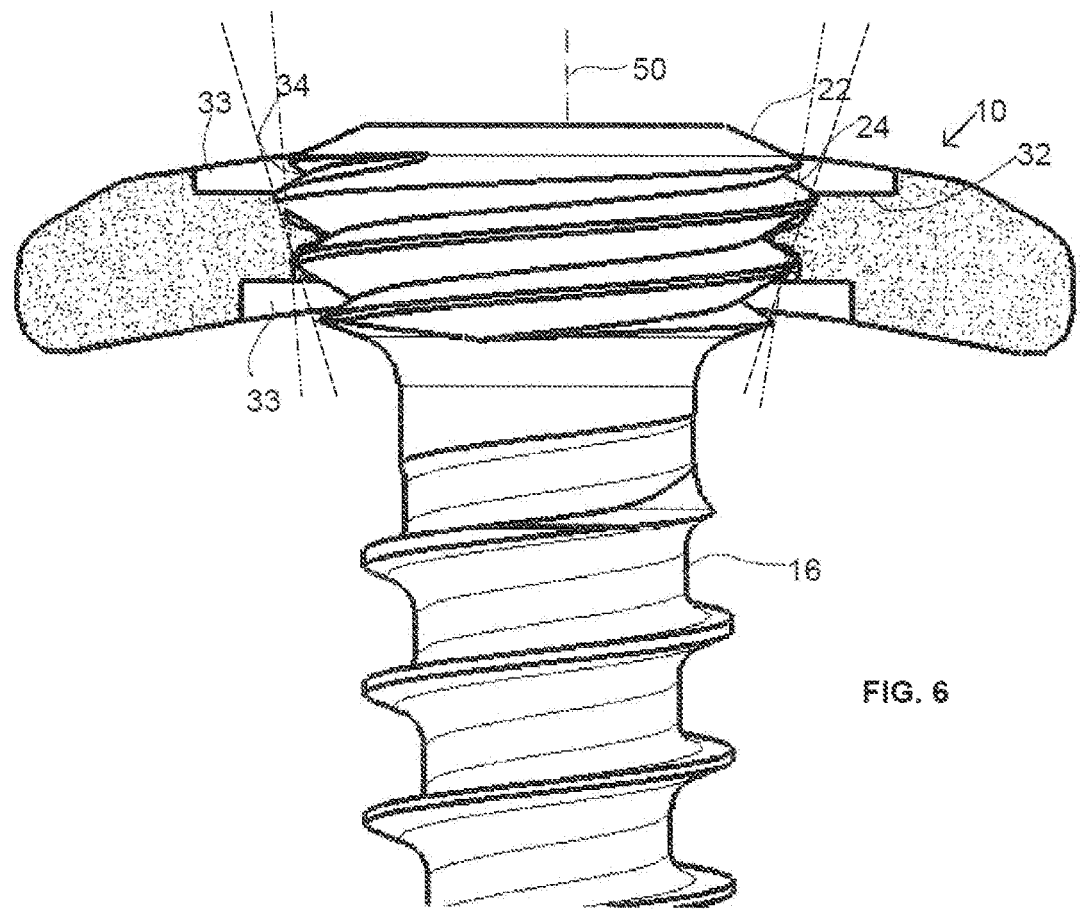
FIG. 6 a detail of the variable locking screw shown at a normal axis orientation in an aperture of the implant of the present invention in cut-away form.

The threads 17 of the annulus 13 of the aperture 14 include one or more recesses 78 (78',79") circumferentially spaced around the annulus 13 so as to define a plurality of threaded sections 79 (78', 79") having at least one thread segment on a section. In an example, the one or more recesses 78 can be formed by creating radially symmetrical hemicylindrical cuts in the internally threaded surface of the threaded aperture 14. Preferably, there are 2-6 recesses, and more preferably 4, 5 or 6 recesses as is illustrated in FIGS. 3-5. The cuts 78, 78' and 78" can have a depth sufficient to completely remove the threads in the area of the recesses such that a substantially smooth recessed surface is created to cause an interruption to the threads crest and at varying degrees to the thread trough such that the vertical edges of the interruptions are not aligned but spiral about the edge of the annulus 13. The effect of the recesses is to form sections with a thread crest 79 and multiple thread troughs on the side wall of the aperture between the recesses. Alternatively, the recess 78 can be formed to a depth that retains the thread segment in the area of the recess 78, albeit at a reduced height (between a root and a crest of the thread) but still sufficient to create the interruption to the thread.

The locking screw head member 22 has a 2-start thread which mates with the female locking threads 17 of the aperture, but the plate's male thread form is sharper (i.e., a 20°-45°, and preferably 30°+/−5° triangular cross-section) than the screw head's female cutout (i.e., a 50°-85°, and preferably 60°+/−10° or 5° triangular cross-section) to facilitate off-axis cross-threading without damaging the threads and so as to avoid generating tailings or metal debris. The locking screw head threads are on a conical taper (smallest diameter at bottom) to facilitate engagement with the plate at various angles and to prevent the screw from being advanced all the way through the plate. To minimize the plate thickness and overall height of the screw/plate assembly over the bone, the underside of the locking screw's head/neck area has a cutting feature which cuts into bone if the screw protrudes too far under the plate. The one or more external threads 20 on the elongate shaft 18 can have double the pitch and the same lead as the locking threads 24 of the head member 22.

Figure 11:
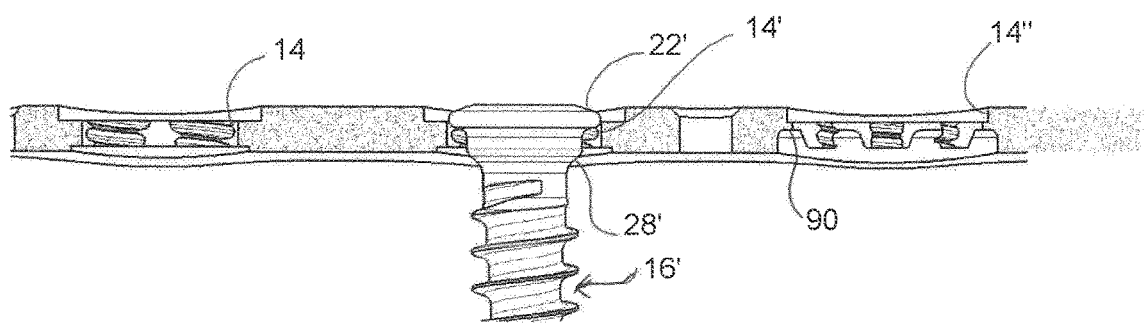
FIG. 11 shows a side view of the implant of the present invention in cross-section, but with a non-locking screw in an on-axis orientation and showing different embodiments of the apertures in the implant.
Figure 12:
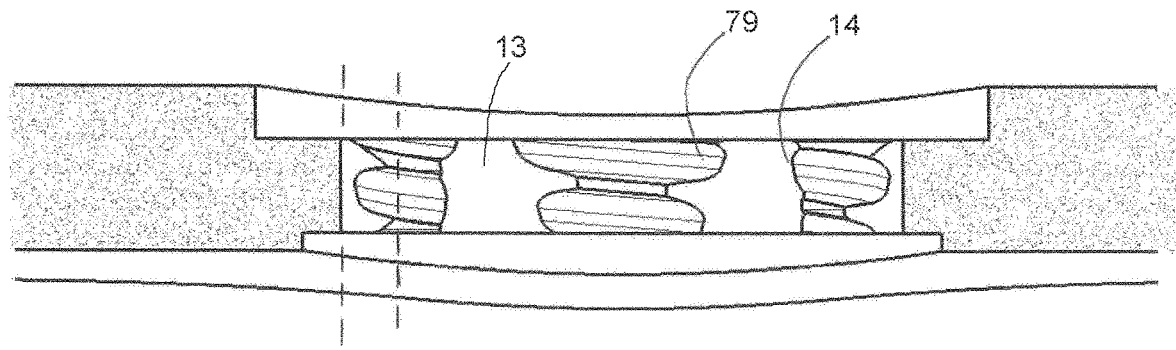
FIG. 12 is a detail illustrating the cylindrical aperture of the implant of the present invention.

FIG. 11 illustrates a non-locking screw 16' in the aperture 14'. In this example, the non-locking screw 16' has a head 22' with a rounded proximal portion that extends into a tapered necked portion 28' which enable the screw to have a wide angle at which it extends through the aperture 14'.

A further embodiment of the implant of the present invention is shown having a trepanned aperture 14". In this embodiment, the aperture includes a concentric outer annular groove 90 which extends vertically up from a surface, and preferably the bottom surface of the implant more that 25%, and preferably more than 50% of the thickness of the implant such that the columns of tabs 79" of threads become independent from the greater plate material to create tines that can flex radially to better accommodate the off-axis external threads of the fastener.

The bone plate 12 and the locking fastener 16 can be formed from any suitable medical-grade material. Exemplary materials can include, but are not limited to, stainless steel, titanium, and cobalt based alloys and coated or anodized versions of these materials. The bone plate 12 and the locking fastener 16 can be formed from the same material or at least partially from different materials.

What is claimed is:

1. An orthopedic implant system, comprising:
a plate including a first surface and a second surface, the plate including at least one aperture, the aperture including one or more female threads which define a thread crest angle T1, and a thread root and at least two recesses within the threads which interrupt the threads to define at least two sections having a thread crest segment and wherein the area of threads comprise areas of thread segments and wherein there is at least one area of thread segments that has no more than two thread segments per area in the direction of the central aperture axis; and
at least one screw including an elongate shaft and a head member having a head configuration including male locking threads, the male locking threads of the head member defining a thread trough angle, T2,
and the male locking threads of the fastener head member and the female threads of the aperture having a differing thread configuration wherein T1 is different to T2 and wherein T2 is from 15° to 45° larger than T1;
wherein the at least one screw is configured for insertion within at least one threaded aperture at a plurality of different insertion angles while achieving a locking engagement between the threaded head and the threaded aperture.

2. The orthopedic implant system as set forth in claim 1, wherein the aperture is a compound opening including an annulus having an annulus configuration and joined to a mouth in at least one of the first surface and the second surface.

3. The orthopedic implant system as set forth in claim 2, wherein the annulus configuration is different from the head configuration.

4. The orthopedic implant system as set forth in claim 3, wherein the annulus configuration is cylindrical and the head configuration decreases in diameter along a vertical axis.

5. The orthopedic implant system as set forth in claim 3, wherein the annulus configuration decreases in diameter along a vertical axis and the head configuration decreases in diameter along a vertical axis at a different rate that the annulus configuration.

6. The orthopedic implant system as set forth in claim 5, wherein the annulus configuration is tapered at an angle of 4° to 20° and the head is tapered at an angle of from 2° and 35° relative to a central axis of the screw or of the aperture respectively.

7. The orthopedic implant system as set forth in claim 1, wherein the annulus configuration is cylindrical and the head configuration decreases in diameter along a vertical axis.

8. The orthopedic implant system as set forth in claim 1, wherein the thread root of the aperture describes a helix.

9. The orthopedic implant system as set forth in claim 8, wherein the thread root defines a helix for at least 120° of the circumference of the aperture.

10. The orthopedic implant system as set forth in claim 9, wherein the thread root defines a helix for at least 180° of the circumference of the aperture.

11. The orthopedic implant system as set forth in claim 1, wherein the helix is cylindrical or tapered and wherein the female locking threads of the aperture have a thread crest that describes a first configuration and the male locking threads of the head member describe a second configuration.

12. The orthopedic implant system as set forth in claim 1, wherein the male locking threads of the screw head are tapered between a proximal end of the threaded head and a distal end of the threaded head.

13. The orthopedic implant system as set forth in claim 12, wherein male locking threads define a conical helix for at least 120° of the circumference of the screw head.

14. The orthopedic implant system as set forth in claim 13, wherein the male locking threads are at least a double lead thread.

15. The orthopedic implant system as set forth in claim 1, wherein there are 2-6 recesses that interrupt the threads.

16. The orthopedic implant system as set forth in claim 1, wherein the value of T2 is at least 1.25× the value of T1.

17. The orthopedic implant system as set forth in claim 1 wherein there is at least one area of thread segments that has no more than one thread segment per area in the direction of the central aperture axis.

18. The orthopedic implant system as set forth in claim 17 wherein there is no area of thread segments that has more than two thread segments per area in the direction of the central aperture axis.

19. An orthopedic implant system with an implant having a threaded aperture with a thread or threads including a thread crest which describe a helix and having from 2 to 6 recesses which interrupt the thread crest in a radially symmetric geometry to form sections of thread segments having a segment of a thread crest and a locking fastener having a head which has a thread or threads including a thread crest that describe a helix and wherein the thread crest of the aperture has an angle T1 which is different than the angle T2 of the thread recess of the screw head and the value of T2 is at least 1.3× the value of T1 and wherein there is at least one area of thread segments that has no more than one thread segment per area in the direction of the central aperture axis.

20. The orthopedic implant system of claim 19, wherein the aperture and the fastener head each has a double lead thread.

21. An orthopedic implant system, comprising:
a plate including a first surface and a second surface, the implant including at least one aperture having a central aperture axis, the aperture including one or more female threads which a have a crest a defining a helical spiral and having a thread crest angle T1, and a thread root and at least two recesses within the threads which interrupt the threads to define at least two areas of thread segments and wherein there is no area of thread segments that has more than two thread segments per area in the direction of the central aperture axis; and
at least one screw including an elongate shaft and a head member along a longitudinal screw axis including male locking threads, the male locking threads of the head member having a thread root defining a conical or hemispherical helical spiral and a thread trough angle, T2, wherein T2 is from 15° to 45° larger than T1;
wherein the at least one screw is configured for insertion within at least one threaded aperture at a plurality of different insertion angles while achieving a locking engagement between the threaded head and the threaded aperture, and the plate thread has a crest, and the plate thread crest forms an interference fit onto the thread root of the screw head member so as to lock the orientation of the screw when the longitudinal screw axis is not co-axial with the central aperture axis, and
wherein the female thread crests of the aperture define a helical spiral that describes a first configuration and the male thread troughs of the screw head define a helical spiral that describes a second configuration and the first configuration is not the same as the second configuration.

22. The orthopedic implant system as set forth in claim 21, wherein the first configuration has a diameter that decreases and the second configuration has a diameter that decreases and the first configuration decreases at a greater rate than the second configuration.

23. The orthopedic implant system as set forth in claim 22, wherein the first configuration is a taper and the second configuration is a taper and the taper of the first configuration has a greater taper angle than the taper of the second configuration.

* * * * *